United States Patent
Griffin

(10) Patent No.: US 7,447,409 B2
(45) Date of Patent: Nov. 4, 2008

(54) SLEEVED OPTICAL FIBER FOR REDUCED LATERAL LOSS AND METHOD FOR MAKING THE SAME

(75) Inventor: Stephen Edward Griffin, Phoenix, AZ (US)

(73) Assignee: AMS Research Corporation, Minnetonka, MN (US)

( * ) Notice: Subject to any disclaimer, the term of this patent is extended or adjusted under 35 U.S.C. 154(b) by 0 days.

(21) Appl. No.: 11/344,371

(22) Filed: Jan. 30, 2006

(65) Prior Publication Data

US 2007/0189683 A1    Aug. 16, 2007

(51) Int. Cl.
*G02B 6/02* (2006.01)
(52) U.S. Cl. ...................................................... 385/123
(58) Field of Classification Search .................. 385/123
See application file for complete search history.

(56) References Cited

U.S. PATENT DOCUMENTS

| | | | |
|---|---|---|---|
| 4,560,247 A * | 12/1985 | Aldebert ..................... 385/124 |
| 5,324,282 A * | 6/1994 | Dodick ......................... 606/15 |
| 5,342,355 A * | 8/1994 | Long ............................. 606/27 |
| 5,343,543 A | 8/1994 | Novak, Jr. et al. |
| 5,428,699 A | 6/1995 | Pon |
| 5,431,647 A | 7/1995 | Purcell, Jr. et al. |
| 5,537,499 A | 7/1996 | Brekke |
| 5,868,734 A | 2/1999 | Soufiane et al. |
| 6,154,595 A | 11/2000 | Yokogawa et al. |
| 6,361,530 B1 | 3/2002 | Mersch |
| 6,576,163 B2 | 6/2003 | Mersch |
| 6,687,445 B2 | 2/2004 | Carter et al. |
| 2004/0069019 A1 | 4/2004 | Carter et al. |
| 2005/0129376 A1 | 6/2005 | Hanson et al. |
| 2006/0285798 A1 * | 12/2006 | Brekke et al. ................. 385/47 |
| 2007/0106280 A1 * | 5/2007 | Utard et al. ............... 604/891.1 |
| 2007/0179485 A1 * | 8/2007 | Yeik et al. ..................... 606/15 |

* cited by examiner

*Primary Examiner*—Ellen Kim
(74) *Attorney, Agent, or Firm*—Jose' W. Jimenez; Kimberly K. Baxter; Gregory L. Koeller

(57) ABSTRACT

A fiber optic, and method for making the same, having glass cladding diameters, or overall glass diameters, or glass-clad sections upon polymer clad fiber, that are large than the bulk of the fiber.

16 Claims, 4 Drawing Sheets

SLEEVED OPTICAL FIBER FOR REDUCED LATERAL LOSS AND METHOD FOR MAKING THE SAME

FIELD OF THE INVENTION

This invention relates generally to applications of silica core optical fiber in lateral delivery of energy pulses or sustained power in surgery, welding and ordinance ignition as well as fiber optic probes for delivering and accepting lateral energy in spectroscopy. The principles outlined herein may also apply to other applications, particularly where minimal distortion of lateral fiber output is critical for delivery of high energy density.

BACKGROUND OF THE INVENTION

In typical axial output fibers, light imparts the fiber output face ideally at angles normal to the fiber axis. Fresnel reflections result from the change in refractive index at the glass/air interface as the light exits the glass and enters the air. Fresnel reflection intensity is proportional to difference between the refractive index of the glass and the surrounding medium and well as to the angle at which the light imparts the interface in refractive indices. Fresnel reflections are at a minimum for light imparting refractive index interfaces normal to the interface plane.

In multimode, large core fibers of the type used in laser energy delivery, the mean angle of the light imparting the axial output face is normal to the fiber axis but the vast majority of the light exiting the fiber does so at angles off of normal to the fiber end plane. Simple lateral output fibers are produced by polishing a bevel on the tip of an optical fiber at an angle off normal to the fiber axis. Light imparting the off-normal polished fiber tip is reflected according to Snell's Law, due to the refractive index interface between the fiber core glass and the surrounding medium, where the angles of incidence for the rays in the fiber meet the conditions for total internal reflection (TIR). Where the surrounding medium is air, the refractive index difference is relatively large so that the off-normal angle of the bevel polish may also be large while accommodating the worst-case light ray angle within the fiber (for fibers or relatively low numerical aperture or relatively low order mode fill). Where the surrounding medium is of a refractive index more closely matching the fiber, the maximum off-normal angle that provides for reflection of all rays within the fiber is reduced proportional to the reduction in refractive index difference. It follows that a bevel tipped silica core fiber (refractive index~1.46), designed for use in air (refractive index 1.00) and providing maximum off axis output will emit at least some light axially. rather than laterally, when immersed in aqueous media (refractive index~∫1.33). Normal contaminants in any use environment may also cause leakage if they come into contact with the reflective bevel tip of a lateral fiber. For this reason, most lateral fibers use a protective cap, positioned about the (angle polished) lateral tip, to exclude moisture and other interfering materials.

The output of surgical lateral fibers is extremely distorted with respect to the output of standard axial fibers. The physical construction of the optical fiber required for delivery of the high energy density is quite different from the construction of optical fiber that is used in communications. Communications fiber is composed of a small, germanium-doped silica core surrounded by a thick, pure silica cladding and the fiber mass is typically composed of less than one percent core material. High energy optical fiber is primarily core material (pure silica), surrounded by a relatively thin, fluorine-doped silica cladding where the core typically represents 70% or more of the fiber mass. The relative thickness of the cladding layer on communications-type fiber is functionally equivalent to an extrapolation of the art disclosed by Pon where the CCDR is roughly 12.5 instead of 1.4. Were such fiber suitable for lateral fiber applications in surgery, the light reflected off a suitable polished bevel tip would impart an approximately flat surface in that the arc of the fiber cylindrical wall inscribed by the beam path is but a small fraction of the fiber circumference such that minimal Fresnel reflection amplification, no Snell reflections and minimal cylindrical distortion would result. Of course, such a CCDR is impractical for the core diameters required in laser surgery; the fiber would be approximately a 7.5 mm diameter rigid rod rather than the required flexible conduit. For fiber constructions suitable for surgical applications, the small CCDRs required give rise to larger portions of the fiber circumference being illuminated by the reflected energy, giving rise to the amplification of Fresnel reflections, the introduction of significant Snell reflections and large cylindrical distortions of the output beam profile.

U.S. Pat. No. 5,562,657 (Griffin) discloses a lateral optical fiber for surgery and ordinance ignition that utilizes a pure silica sleeve, fused about fluorine-doped silica clad, silica core optical fiber (abbreviated "silica:silica" fiber in the industry) for the purpose of permitting laser-forming of the reflective bevel tip and shielding against melt distortion in subsequent fusion of the beveled and sleeved fiber to a protective silica cap.

U.S. Pat. No. 5,428,699 (Pon) discloses a high cladding-to-core diameter ratio (CCDR) fluorine-doped silica:silica fiber for lateral output surgery where the additional fluorine-doped cladding thickness reduces the reflections and distortions within the lateral output of the fiber upon which a reflective bevel tip has been formed. Pon does not anticipate fusion of the heavily clad fiber within a protective silica cap but disposes the bevel tip loosely within the cap.

U.S. Pat. No. 5,537,499 (Brekke) discloses a silica:silica optical fiber for lateral output surgery where the fiber cladding is directly fused to the protective silica cap just within the area of the light output.

Pon address the issues of unwanted Snell reflections, Fresnel reflections and cylindrical distortions within the output of lateral fibers. These distortions and reflections are primarily a result of light exiting the optical fiber through the sidewall rather than through a flat surface that is orthogonal to the mean axis of light propagation within the fiber, as in standard, axial output fibers. The magnitude of Fresnel reflections and cylindrical distortions is dependent upon the off-normal angles at which the light rays traverse the refractive index barrier upon exiting the fiber. By increasing the overall diameter of the fiber (beyond what is optically necessary for axial light propagation through the fiber), the angular arc portion of the fiber circumference through which the light passes in reduced, reducing angle dependent Fresnel reflections. Increasing the effective focal length of the cylindrical lens formed by the fiber sidewall also reduces cylindrical distortions, but most importantly the majority of the rays reflected by the bevel tip impart the fiber sidewall at angles close enough to normal to evade total internal reflection as governed by Snell's law.

In Griffin and Brekke, eliminating the air space between the fiber cladding and the protective cap entirely minimizes the refractive index difference within the light path, thereby minimizing all reflections and distortions. In Griffin, the fiber cladding is fused within a silica sleeve that is, in turn, fuse within the protective cap. In Brekke, the fiber cladding is directly fused to the protective cap. The effective diameter of the fiber at the output, in both approaches, becomes the cap diameter, which is typically a great deal larger than the original fiber cladding diameter. Further, in surgery, the fibers are used in aqueous media such that the final refractive index barrier traversed by the emitted light is from silica (1.46) to water (1.33). Where this minimal distortion is problematic, as is applications in lower refractive index media, Griffin disposes a flat surface on the output cap normal to the output axis.

Brekke is extremely similar to Griffin but in Brekke the fiber cladding itself is spot fused to the cap just on the fiber side surface where the light exits, eliminating most reflections and distortions. As a practical matter, the act of fusing a bare fiber into a relatively massive protective cap melts the reflective surface slightly, resulting in some distortions in the initial reflection. Pon avoids distorting the reflective bevel face at the expense of some reduction in Fresnel reflections and cylindrical distortions in that an air gap remains between the fiber cladding and the cap inner wall.

While the reduction of distortions in Brekke and Griffin are far superior to that afforded by Pon, there is an unrelated advantage provide by the art disclosed by Pon. Particularly in applications where energy densities within the fiber are especially high and where the light acting upon the target produces great amounts of heat, for example in pulse laser surgical applications, the fused strategies disclosed by Griffin and Brekke fail due to rapid thermal expansion and contraction. The fusion processes result in local stresses within the composite silica structures that are prone to fracture when exposed to extreme temperature differences. In short, the total energies that may safely be used within the art disclosed by Brekke and Griffin are limited due to these residual stresses. The art according to Pon is far more robust in extreme applications.

The art disclosed in Pon is practically limited by the minimal options available in fiber CCDR (as well as other dimensional design constraints) to a fiber cladding diameter that is 1.4-fold the core diameter. The fibers described in Pon as the preferred embodiment have 400 µm and 600 µm cores and, while non-standard, are drawn (produced) from standard preforms, though typically rare and expensive. A 1.6 CCDR fiber would perform better than the 1.4 CCDR fiber disclosed in Pon, but the costs of producing such fiber are incompatible with the needs of the surgical application because the 1.6 CCDR preforms required are non-standard and would be extremely costly to produce. The art in Pon is, in fact, limited by these economic considerations. 1.4 CCDR fiber costs more than twice as much to produce as the standard, 1.1 CCDR fibers disclosed in Griffin and Brekke and more than ten-fold more than the alternative disclosed herein. Further, use of larger CCDR fiber throughout a device limits the flexibility wherein flexibility is desirable.

In that the costly 1.4 CCDR fiber is only required within the relatively short lateral output portion of the surgical device (~1 mm of an ~3 m assembly), efforts have been made to splice short sections of 1.4 CCDR fiber to lower cost fibers. Unfortunately, where communications optical fiber is extremely precise in core and cladding dimensions (with a dimensional tolerance of less than 1% on relatively small overall diameters, typically 125 µm), the dimensions of the large core, multimode fiber used in surgical devices is less reproducible at typically 2% tolerance on the cladding diameter. Fusion splices in telecommunications-type fiber are fairly simple and routine, owing to the precise and accurate dimensions of the fiber. Further, given the standard variability in CCDR of 0.02 that is typical for power transmission-type fibers, coupled with the imprecision in maintaining overall fiber (cladding) dimensions, the core diameters may vary by as much as 4% between production lots of fiber in the diameters of interest. Mating cores that vary by as much as 25 µm between the low cost, 1.1 CCDR fiber and the costly 1.4 CCDR fiber introduces severe complications. The severe mismatch in glass diameters between the low cost fiber and the high CCDR fiber introduces additional difficulties in producing efficient fusion splices.

Where the laser wavelengths of interest are permitting, the use of polymer clad silica for carrying the energy to the lateral tip eliminates the variability of the CCDR presented by silica:silica fibers, but the core dimensional mismatch problem is reduced by approximately 50%: it is not eliminated. Where the low cost, trunk fiber under fills the receiving 1.4 CCDR fiber section, the dimensional mismatch problem is minimal in that all of the light exiting the trunk fiber enters the core of the short, lateral emission section. Where the inverse is the case, light exiting the larger trunk core will enter the 1.4 CCDR fiber (lateral emission section) cladding, rendering the Fresnel and Snell reflection reduction strategy ineffective for these cladding modes.

One strategy for eliminating the possibility of over-filling the receiving fiber core is to produce the 1.4 CCDR fibers at slightly larger than "normal" dimensions, rendering the minimum core diameter that is possible larger than the maximum trunk fiber core possible. Similarly, one could produce the lower cost trunk fiber to smaller than normal dimensions. This strategy preserves the reflection reduction strategy but introduces new complications in device design by increases the physical dimension mismatch issues and the overall size of the lateral emissions section by ~4% or reducing the available core diameter for input of the laser energy. Beyond dimensional mismatch of the trunk and lateral emission section cores, precise physical alignment of the cores is also necessary and physical alignment of extremely different diameter materials is far more challenging that matching identical diameters.

The use of polymer clad silica fiber is attractive from cost perspectives. A solution for forming high CCDR, silica:silica fiber sections on low cost, silica:silica or polymer clad silica fiber, that evades dimensional mismatch problems, would be of considerable utility.

SUMMARY OF THE INVENTION

The invention claimed and described herein comprises a strategy for forming short sections of high CCDR, fluorine-doped silica clad:silica core fiber (silica:silica fiber) upon either lower CCDR silica:silica fiber or upon polymer clad silica fiber. In the preferred embodiment, a tube formed of uniformly fluorine-doped silica is produced that possesses dimensions similar to the desired fiber cladding wherein the core is eliminated, where the fluorine concentration is equivalent to standard fiber cladding. A polymer clad fiber is stripped of cladding for a short length at one terminus. The relatively close fitting, fluorine-doped tube is positioned over the bare core and is fused into place entirely about the circumference of the fiber by thermal collapse, effectively forming a section of silica:silica fiber.

Alternatively, the base fiber may be a lower CCDR fiber upon which it is desirable to have a section of larger CCDR. In this case, the fluorine-doped tube is of outer diameter approximately equivalent to the desired outer diameter of the thicker clad (higher CCDR) fiber section and the inner diameter is slightly larger than the trunk fiber cladding. Any polymer coatings or buffers upon the trunk fiber are removed for a short section at one terminus. The fluorine-doped tube is positioned over the bare cladding of the trunk fiber and is fused into place about the entire circumference, forming a short section of higher CCDR fiber upon a low CCDR trunk fiber.

Where the trunk fiber is low CCDR, silica:silica fiber, the tube may be composed of non-doped silica or silica doped with less than standard concentrations of fluorine because the bulk fiber core will be preserved by the existing fluorine-doped silica of the trunk fiber, through the overclad section. The light exiting the fiber through a composite wall of this construction will experience some distortions in excess of the preferred embodiment due to the additional refractive index barrier thus produced, but the additional output distortions are minimal and may be acceptable in some applications.

The art disclosed herein offers flexibility in fiber design in addition to cost reduction and ease of execution. Where a fusion spliced version of Pon may only be made using the few fiber CCDRs that are offered commercially—1.05, 1.1, 1.2 and 1.4—the fluorine-doped or pure silica tubing disclosed herein may be made to virtually any dimensions imaginable, at very low cost. Further in contrast to prior art, the invention disclosed herein provides all of the reductions in reflections and cylindrical distortions of Pon while using low cost fiber in a manner where core and dimensional mismatch issues are eliminated.

Griffin discloses silica tubes disposed over stripped sections of silica:silica fiber for providing an increased diameter upon which laser-formed bevel tips may be produced and fused within protective caps. The use of lasers to form bevel reflectors are desirable for affording speed and uniformity in production, high damage threshold, and resistance to damage upon insertion into caps. The fiber edge rounding that provides the resistance to damage is finite and must not extend into the core region or distortions will occur in the fiber output due to non-planarity of the reflective face. The art disclosed in Pon also presents an increased diameter but the limits imposed in the overall diameter to core ratio (1.4 as a practical maximum) may be insufficient to permitting laser-formed bevels absent rounding in the core region within some fiber dimensions. The art disclosed herein is not so limited.

Among the objects of the present invention are the following:

To provide a new and useful method of producing sections of fluorine-doped silica clad fiber upon polymer clad silica fiber;

To provide a new and useful method of producing sections of fiber possessing thicker fluorine-doped silica cladding that the bulk of a fluorine-doped silica clad, silica core fiber;

To provide a new and useful method of producing sections of larger glass diameter upon fluorine doped silica clad, silica core fiber;

To provide a new and useful construct upon which lateral diversion elements may be produced upon optical fiber that offer reduced reflection and cylindrical distortion.

The novel features that are considered characteristic of the invention are set forth with particularity in the appended claims. The invention itself, however, both as to its structure and its operation together with the additional objects and advantages thereof will best be understood from the following description of the preferred embodiment of the present invention. Unless specifically noted, it is intended that the words and phrases in the specification and claims be given the ordinary and accustomed meaning to those of ordinary skill in the applicable art or arts. If any other meaning is intended, the specification will specifically state that a special meaning is being applied to a word or phrase. Likewise, the use of the words "function" or "means" in the Description of Preferred Embodiments of the invention is not intended to indicate a desire to invoke the special provision of 35 U.S.C. §112, paragraph 6 to define the invention. To the contrary, if the provisions of 35 U.S.C. §112, paragraph 6, are sought to be invoked to define the invention(s), the claims will specifically state the phrases "means for" or "step for" and a function, without also reciting in such phrases any structure, material, or act in support of the function. Even when the claims recite a "means for" or "step for" performing a function, if they also recite any structure, material or acts in support of that means of step, then the intention is not to invoke the provisions of 35 U.S.C. §112, paragraph 6. Moreover, even if the provisions of 35 U.S.C. §112, paragraph 6, are invoked to define the inventions, it is intended that the inventions not be limited only to the specific structure, material or acts that are described in the preferred embodiments, but in addition, include any and all structures, materials or acts that perform the claimed function, along with any and all known or later-developed equivalent structures, materials or acts for performing the claimed function.

DESCRIPTION OF THE PREFERRED EMBODIMENT

Figure 1:
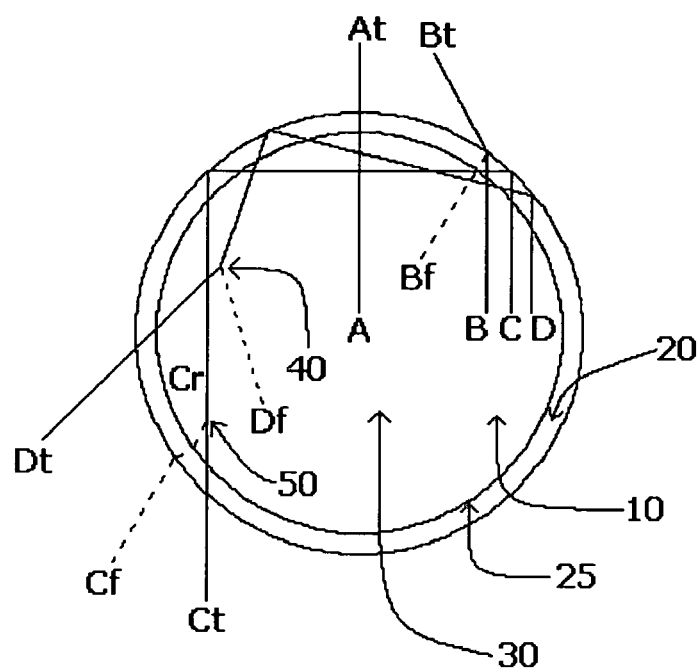
FIG. 1 is an end view in partial section of the standard art of lateral fibers, depicting the fate of four rays reflected from the bevel surface.
Figure 2:
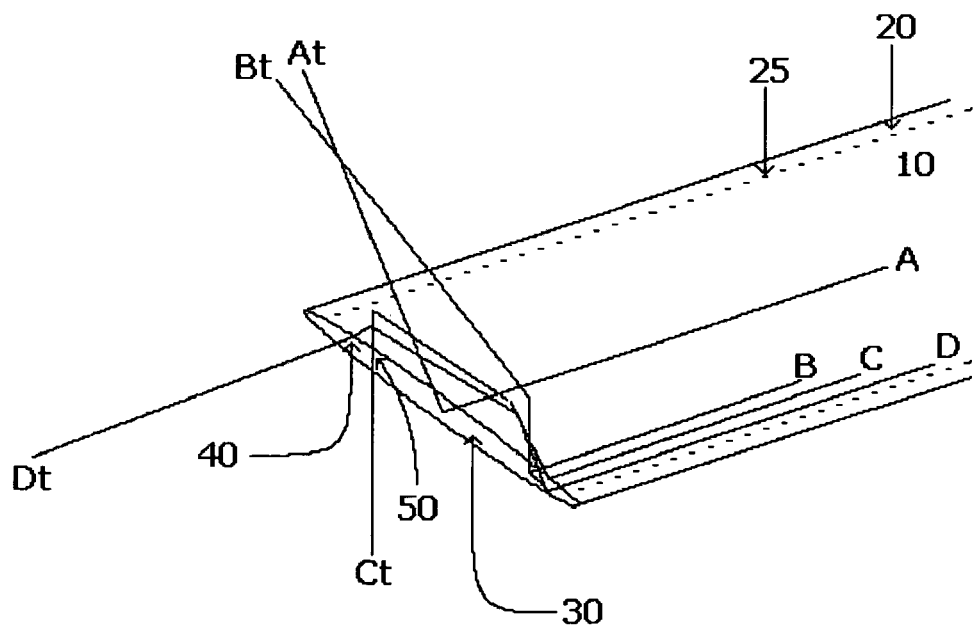
FIG. 2 is perspective view of the standard art in FIG. 1, providing an alternative view of the fate of the four reflected rays.

FIGS. 1 and 2 should be referred to in unison for clarity in tracing the paths of some characteristic rays within the output tip of a standard lateral fiber. The figures depict the fate of four rays, A, B, C and D that have been conducted to the beveled fiber face 30 within a standard, 1.1 CCDR fiber where the fiber core 10 of diameter X is surrounded by fluorine-doped cladding 20 of diameter 1.1X. All rays depicted are chosen to be zero order within the transmitting fiber for simplicity. In reality the extreme cases are more extreme than depicted due to the fact that higher order (angle) rays are supported within the transmitting fiber. Ray A is centered within the fiber core 10 and represents the best-case ray for the fiber design, for reference. The angle of incidence upon the fiber sidewall for ray A is essentially normal to the plane of the circumference so that the transmitted ray At is minimally refracted, there are no reflections according to Snell's Law and Fresnel reflections are also near minimum. Ray B is imparts the reflective bevel face 30 off-center and is reflected to the fiber sidewall off-center, where the contact angle is lower than (off-normal) that for more centered rays but too high to be reflected according to Snell's Law. Some portion of ray B is reflected (Fresnel) as Bf but the majority of the energy is refracted through the fiber wall as ray Bt.

Rays C and D impart the bevel face 30 even closer to the edge of the fiber such that the angles of incidence upon the glass-to-air interface are lower than those required for total internal reflection as defined by Snell's Law. Both rays are entirely reflected within the fiber, taking on a corkscrew path akin to a meridial mode until the rays reach the bevel face again, at points 40 and 50, respectively, where they are refracted as Ct and Dt as they pass into the air. Some Fresnel reflections, Cf and Df, necessarily result upon exit of the rays.

Figure 3:
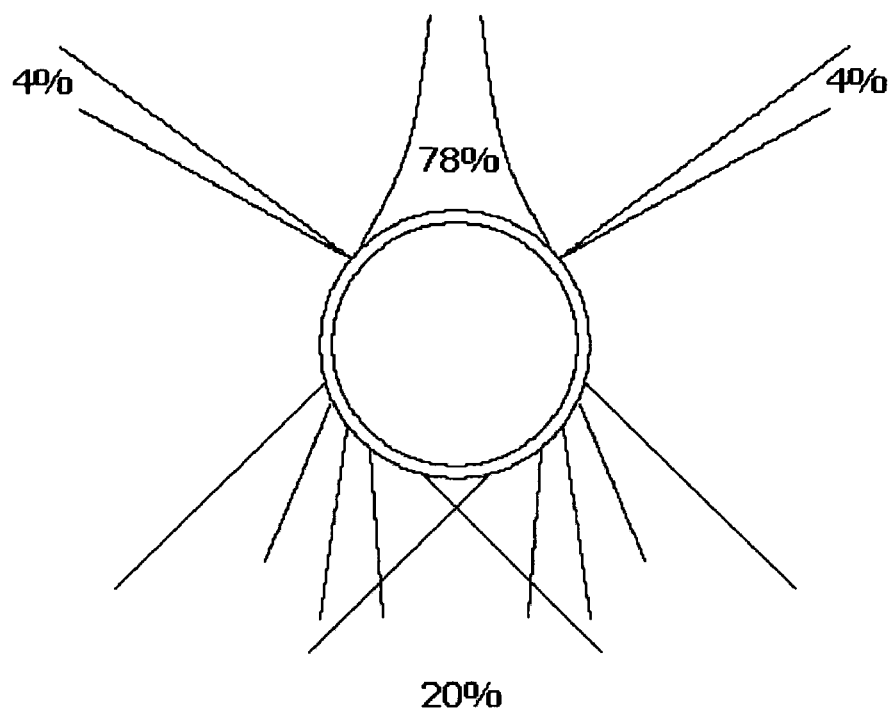
FIG. 3 depicts the average output pattern of a standard, 0.22 NA, 1.1 CCDR lateral fiber.

When all possible rays within the fiber are summed, the result is an extremely complex pattern of reflections and refractions. For a 0.22 NA fiber at 1.1 CCDR, the best case net result is approximately 72% of the light is directed off the fiber axis in the direction desired while approximately 8% of the light escapes at wider angles generally within the desired output direction and approximately 20% of the energy escapes in directions essentially opposite that desired. FIG. 3 depicts this general pattern.

Figure 4:
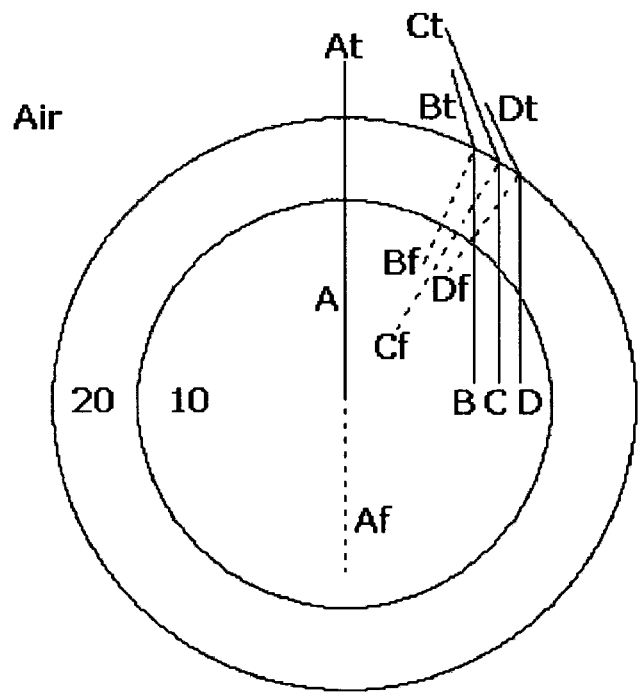
FIG. 4 is an end view in partial section of the prior art described by Pon, depicting the fate of the same four rays as shown in FIGS. 1 and 2.

FIG. 4 depicts the same four rays within the art described by Pon where the increased fiber diameter causes all of the rays, A, B, C and D, to impart the fiber side wall at angles exceeding those required for total internal reflection (according to Snell's Law) such that the rays are all refracted across the refractive index barrier in the general direction desired as At, Bt, Ct and Dt. Some minimally amplified Fresnel reflections remain as depicted by the broken lines labeled Af, Bf, Cf and Df. In practice, where the worst-case rays exceed those depicted in FIG. 4, the art disclosed by Pon results in >90% of the rays imparting the arc of the enlarged fiber sidewall at angles that do not invoke Snell's Law mediated reflections.

The first four Figures serve as background depicting the value of the prior art disclosed by Pon and as reduced to practice in the ADD-Stat™ lateral fiber as used in the GreenLight™ PVP™ procedure for treating enlarged prostate glands (trademarks of Laserscope Surgical Systems, Inc.). Pon goes on to describe additional variants that are not currently in production, many of which are impractical to produce, such as triangular cross-section optical fiber, "race track" semi-oval cross-section fiber, etc. Most of these variants involve providing a flat plane for output in place of the curved arc of circular cross-section fiber. The fundamental limitation of the claims is that greater than about 90% of the light reflected from the polished bevel intersects the output surface of the fiber at angles greater than that required for total internal reflection as embodies by the 1.4 CCDR fiber embodiment.

The invention described herein seeks to provide a more cost effective means of achieving the advantages disclosed in Pon. Attempts have been made to lower the costs of producing fibers based upon Pon by fusion splicing a short segment of the high cost, high CCDR fiber to lower cost, polymer clad or lower cost, low CCDR fibers. It is apparent to those skilled in the art that this solution raises separate cost and execution issues as described in some detail above. In brief, dimensional variations in fiber core diameters combined with the physically mismatched outer glass diameters of the two fiber types present major problems in producing this hybrid fiber. A fusion splice is absolutely required at the energy densities of the intended use but core misalignments and the dimensional mismatch complicates production of such splices. Further, the art described in Pon is practically limited to certain fixed ratios of core and cladding because only those ratios are commercially produced as fiber preforms (from which the bulk fiber is drawn).

Where the trunk fiber (the bulk of the hybrid fiber that communicates the laser output to the lateral redirecting tip) overfills the high CCDR fiber due to misalignment or dimensional mismatch, light will be introduced into the glass cladding that surrounds the silica:silica fiber section core. This light is may expand to fill a larger portion of the polished reflector than is intended such that less than 90% of the reflected light intersects the curved fiber sidewall at angles greater than those for total internal reflection, rendering the art ineffective. Angular misalignment of the two fiber section would result in other problems such as angular overfill of the polished bevel surface that results in axial leakage, skew ray generation at the bevel tip, etc.

The dimensional (fiber outer diameter) mismatch results in preferential flow of glass from the larger fiber diameter to the smaller fiber diameter in the melt condition produced during the fusion splice operation. This flow of glass can result in core distortions that adversely affect the uniformity of the light transmission through the splice; light scatters from the splice or is altered in propagation angle, resulting in unpredictable lateral redirection performance.

A mechanism for forming a high CCDR fiber section upon existing low CCDR fiber or polymer clad fiber is desirable in that core-to-core and segment-to-segment misalignment issues are avoided. Because the core is contiguous through both sections, no mismatch or misalignment is possible. The art disclosed herein accomplishes this goal.

Figure 5:
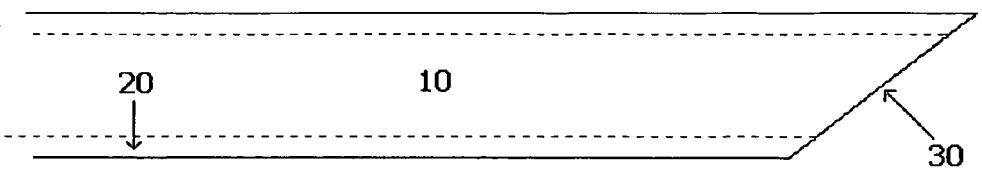
FIG. 5 is a side view in partial section taken generally along the centerline of the fiber depicted in FIG. 4.

FIG. 5 a view in partial section along the axis of the reflective tip disclosed in Pon. The entire fiber length is homogeneously composed of a core 10 of dimension X and a surrounding cladding 20 of dimension 1.4X and the reflective bevel surface 30 is polished directly upon the optical fiber that communicates laser energy to the tip at an angle designed to afford total internal reflection of all possible ray angles incident upon the bevel.

Figure 6:
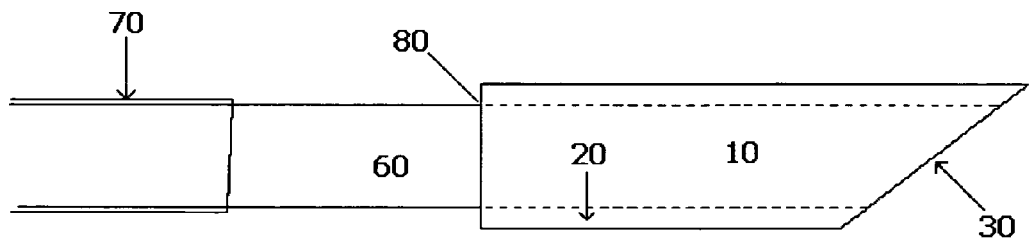
FIG. 6 is a side view in partial taken generally along the centerline of the fusion-spliced modification of Pon.

FIG. 6 is the same view in partial section of the fusion spliced fiber hybrid. The same 1.4 CCDR fiber is employed for the critical lateral redirection function, with X dimensioned silica core 10 and 1.4 dimensioned fluorine-doped silica cladding 20 and the same polished bevel reflector 30 formed thereupon, but the bulk of the fiber device, the portion dedicated to communicating the laser energy to the lateral tip, is silica core 60 fiber clad with a low refractive index polymer 70. The polymer clad trunk fiber is fusion spliced to the short 1.4 CCDR section at 80. The Figure is simplified and idealized for clarity; in practice the transition from polymer clad fiber to the 1.4 CCDR fiber is less abrupt due to melt flow of the glasses.

Figure 7:
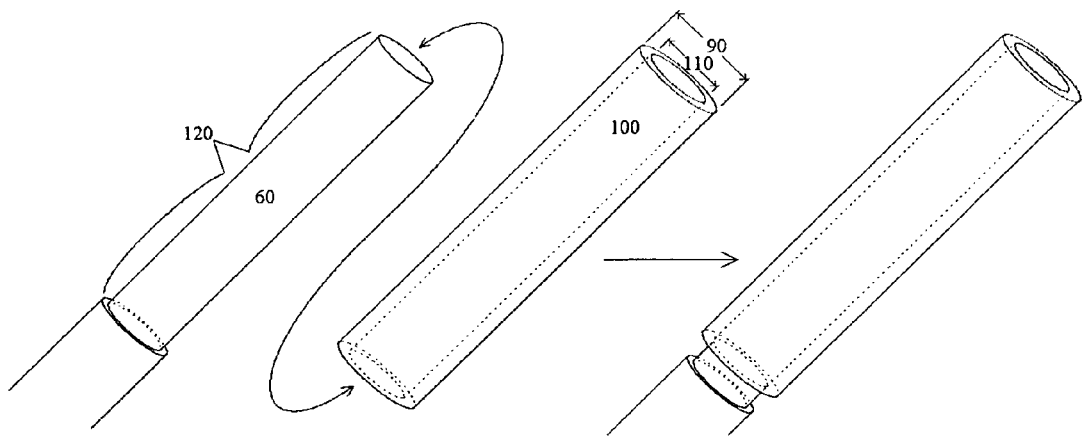
FIG. 7 is perspective assembly diagram for the art disclosed herein.
Figure 8:
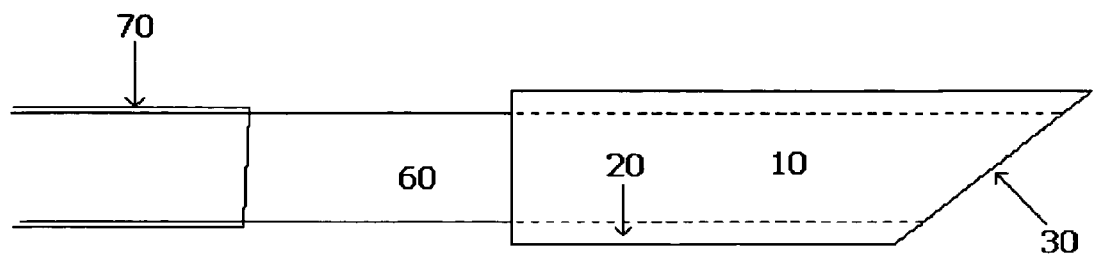
FIG. 8 is a side view in partial section generally taken along the centerline of the art disclosed herein as it results for the assembly process depicted in FIG. 7.

FIG. 7 is a perspective view of the art disclosed herein, illustrating the components and the resulting assembly. A section of fluorine-doped tubing 100, possessing an inner diameter 110 that is slightly larger than the polymer clad fiber's silica core 60 and an outer diameter 90 that is approximately the same as the outer diameter of the corresponding 1.4 CCDR fiber in FIGS. 5 and 6 (solely in the case of replication of prior art) is disposed over a bare (of polymer cladding) terminal section 120 of the polymer clad fiber. Heat is applied to the circumference of the fluorine-doped tube, shrinking it and fusing it about the terminal section of the polymer fiber core 120, converting this overclad region into 1.4 CCDR fiber. Finally, the reflective bevel tip is formed upon the 1.4 CCDR fiber section resulting in the view in partial section depicted in FIG. 8. Note that the diagram in FIG. 8 is indistinguishable from the diagram in FIG. 6 but in contrast to the art depicted in FIG. 6 there is absolutely no chance of core mismatch or misalignment in the construct as formed in FIG. 8.

Some laser wavelengths, such as those in the ultraviolet and mid-infrared regions of the spectrum, are better served by the use of fluorine-doped silica clad, silica core fiber. In these cases, lower CCDR fiber, for example 1.05 CCDR, may be similarly sleeved with fluorine-doped silica tubing as shown in FIG. 7. One might also chose to employ pure silica tubing in place of the more costly fluorine-doped silica tubing in these cases in that the core integrity is maintained by the continuous fluorine-doped cladding throughout the construct. Because the tubing may be drawn to any dimensions desired, the option for higher effective CCDR sections in open to the designer and such options remain economical such that the limitation of the art disclosed by Pon, where "greater than approximately 90% of the reflected light" imparting the fiber sidewall at angles greater than those required for total internal reflection is no longer a limitation: approximately 100% evasion of TIR at the fiber sidewall is within easy reach of the art disclosed herein.

The preferred embodiment of the invention is described above in the Description of Preferred Embodiments. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of a preferred embodiment and best mode of the invention known to the applicant at the time of filing the application has been presented and is intended for the purposes of illustration and description. It is not intended to be exhaustive or to limit the invention to the precise form disclosed, and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated.

What is claimed is:

1. A fiber optic comprising a short section of fluorine-doped tubing fused about a terminal end of a polymer clad, silica core fiber where a reflective bevel is polished on a terminal end of the fused section for the purpose of redirecting light laterally with respect to the fiber axis.

2. A fiber optic comprising a short section of fluorine-doped tubing fused about a terminal end of a fluorine-doped silica clad, silica core fiber, where a reflective bevel is polished on a terminal end of the fused section for the purpose of redirecting light laterally with respect to the fiber axis.

3. A fiber optic comprising a short section of pure silica tubing fused about a terminal end of a fluorine-doped silica clad, silica core fiber where a reflective bevel is polished on a terminal end of the fused section for the purpose of redirecting light laterally with respect to the fiber axis.

4. The fiber optic according to claim 1 where the dopant in the tubing is uniform throughout.

5. The fiber optic according to claim 2 where the dopant in the tubing is uniform throughout.

6. The fiber optic according to claim 1 where the dopant in the tubing varies in concentration within the radius of the tubing.

7. The fiber optic according to claim 2 where the dopant in the tubing varies in concentration within the radius of the tubing.

8. The fiber optic according to claim 1 where the dopant in the tubing varies in concentration along the axis of the tubing.

9. The fiber optic according to claim 2 where the dopant in the tubing varies in concentration along the axis of the tubing.

10. The fiber optic according to claim 2 where a reflective bevel is polished on a terminal end of the fused section for the purpose of redirecting light laterally with respect to the fiber axis.

11. The fiber optic according to claim 1 wherein the bevel tipped fiber is further disposed within a protective silica cap.

12. The fiber optic according to claim 10 wherein the bevel tipped fiber is further disposed within a protective silica cap.

13. The fiber optic according to claim 3 wherein the bevel tipped fiber is further disposed within a protective silica cap.

14. The fiber optic according to claim 11 where the fiber conducts light from a laser to the terminal end for the purpose of treating tissues in surgery.

15. The fiber optic according to claim 12 where the fiber conducts light from a laser to the terminal end for the purpose of treating tissues in surgery.

16. The fiber optic according to claim 13 where the fiber conducts light from a laser to the terminal end for the purpose of treating tissues in surgery.

* * * * *